(12) United States Patent
McElligott

(10) Patent No.: US 6,613,287 B1
(45) Date of Patent: Sep. 2, 2003

(54) CEILING FAN BLADE AIR FRESHENER

(76) Inventor: Frank G. McElligott, 1550 Meadows Cir., Rockwall, TX (US) 75087

( * ) Notice: Subject to any disclaimer, the term of this patent is extended or adjusted under 35 U.S.C. 154(b) by 137 days.

(21) Appl. No.: 09/611,058

(22) Filed: Jul. 6, 2000

(51) Int. Cl.⁷ .................................................. A61L 9/12
(52) U.S. Cl. ............................ 422/124; 416/62; 239/57
(58) Field of Search ........................... 422/5, 124, 266; 416/62; 53/134.2; 426/82, 83; 239/57

(56) References Cited

U.S. PATENT DOCUMENTS

| | | | |
|---|---|---|---|
| 1,491,407 A | * 4/1924 | Jordan | |
| 4,666,670 A | * 5/1987 | Cox | 422/124 |
| 4,743,406 A | 5/1988 | Steiner et al. | 261/30 |
| 4,808,347 A | 2/1989 | Dawn | 261/30 |
| 4,892,460 A | 1/1990 | Volk | 416/62 |
| 4,957,246 A | * 9/1990 | Kantor | 242/55.53 |
| 5,022,819 A | * 6/1991 | Murcin et al. | 416/62 |
| 5,087,273 A | * 2/1992 | Ward | 422/5 X |
| D324,910 S | 3/1992 | Portis | D23/366 |
| D324,920 S | * 3/1992 | Portis | D23/366 |
| D334,800 S | 4/1993 | Portis | D23/366 |
| 5,210,396 A | * 5/1993 | Sanders | 219/521 |
| 5,383,765 A | * 1/1995 | Baxtor et al. | 416/62 |
| 5,564,900 A | 10/1996 | McAuley | 416/62 |
| 5,567,361 A | 10/1996 | Harper | 261/26 |
| 5,624,230 A | 4/1997 | Taylor et al. | 416/5 |
| 5,698,166 A | 12/1997 | Vick et al. | 422/124 |
| 5,833,929 A | 11/1998 | Watson et al. | 422/123 |
| 5,891,391 A | * 4/1999 | Fore | 422/124 |
| 5,935,526 A | * 8/1999 | Moore | 422/124 |
| 6,032,930 A | 3/2000 | Calino | 261/26 |

* cited by examiner

*Primary Examiner*—Elizabeth McKane
(74) *Attorney, Agent, or Firm*—F. Lindsey Scott

(57) ABSTRACT

An air freshener for attachment to a ceiling fan blade. The air freshener includes an open mesh pouch position on the ceiling fan blade and adapted to contain an air freshening material so that when the blade is rotated air is passed over and through the air freshening material.

11 Claims, 2 Drawing Sheets

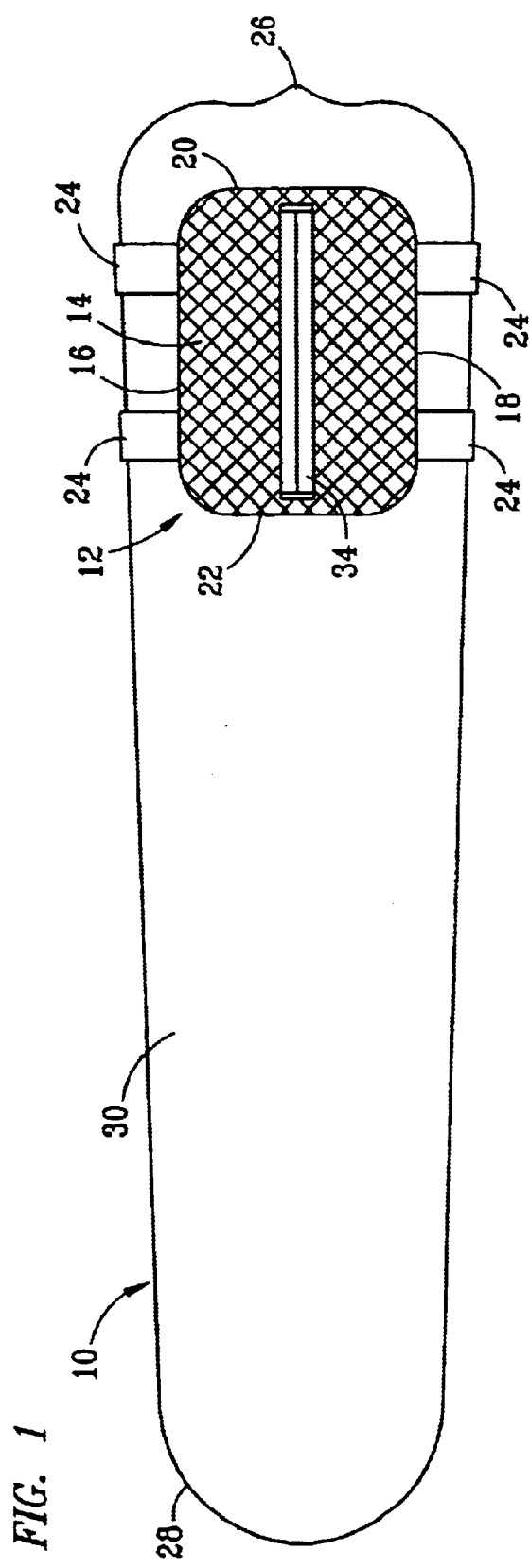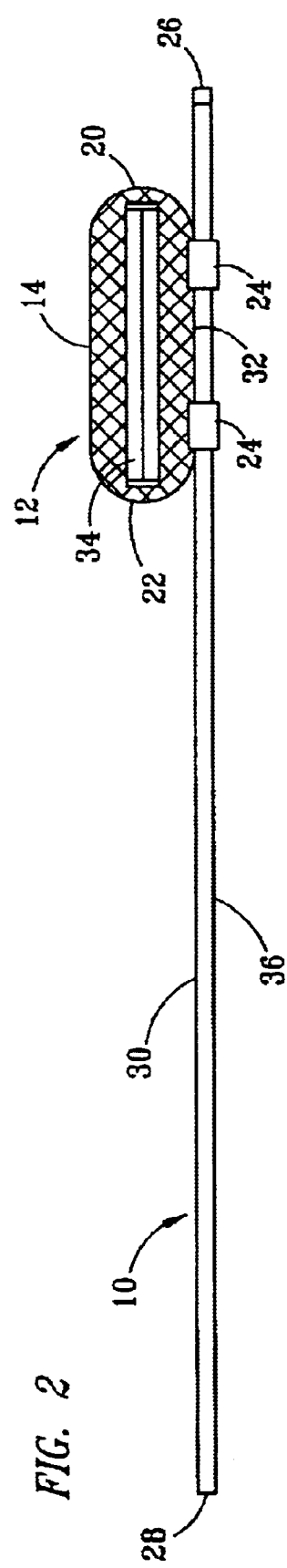

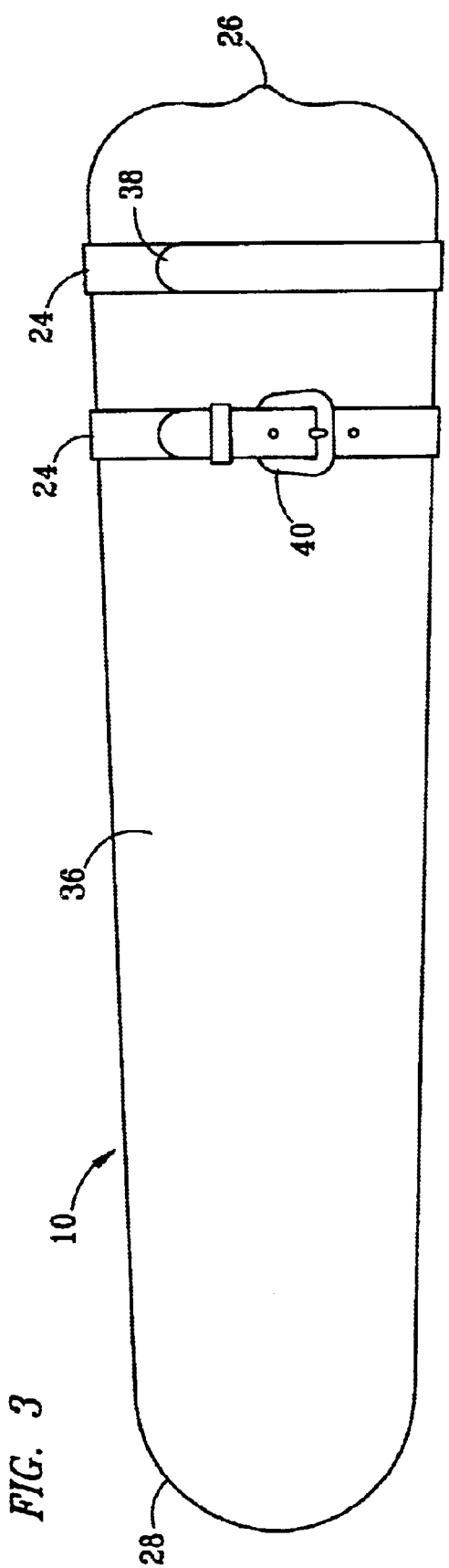
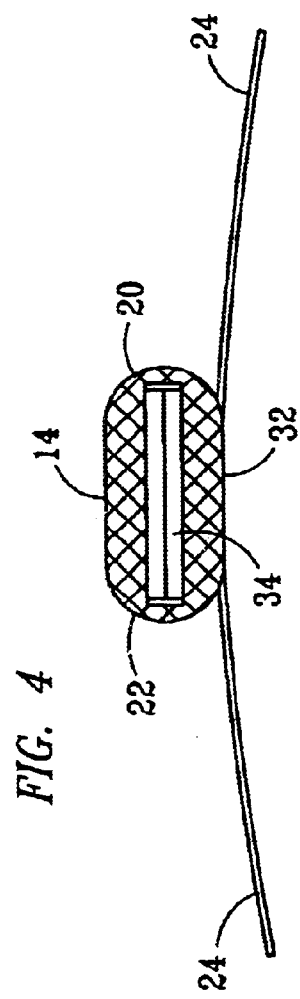
FIG. 3
FIG. 4

CEILING FAN BLADE AIR FRESHENER

FIELD OF THE INVENTION

This invention relates to an air freshener for attachment to a ceiling fan blade comprising an open mesh pouch positioned on the ceiling fan blade and containing an air freshener material so that air passing over and through the air freshener material in the open mesh pouch by operation of the ceiling fan.

BACKGROUND OF THE INVENTION

Many approaches have been used in attempts to position air freshening materials in containers positioned on ceiling fan blades, ceiling fan pull chains, ceiling fan hubs and the like. Many of these approaches use fixed walled containers or containers, which require specially configured air freshening material, cartridges, particles, or the like. Other approaches use systems which require the use of heat, auxiliary fans and the like. Many of these systems require relatively expensive fixtures, which are relatively awkward to maintain in position and recharge and the like.

Since ceiling fans are widely used and since in many instances it is desirable to use air fresheners to provide a pleasant fragrance or to cover an unpleasant odor in a room having a ceiling fan, a continuing effort has been directed to the development of more economical, more effective and more easily used air fresheners for use with ceiling fans.

SUMMARY OF THE INVENTION

According to the present invention, it has been found that a fragrant air freshening material is readily used to create a fragrance in the air in a room by the use of an air freshener for attachment to a ceiling fan blade. The air freshener comprises an air freshener for attachment to a ceiling fan blade, the air freshener comprising a flexible walled open mesh pouch having a front and a back, a first and a second side and a first and a second end, the pouch being adapted to contain a quantity of a fragrant air freshening material; at least one retaining strap in restraining engagement with the pouch and adapted to retain the pouch in a selected position on a ceiling fan blade; and an openable and closable opening in at least one of the front, back, first side, second side, first end and second end.

BRIEF DESCRIPTION OF THE DRAWINGS

FIG. 1 is a top view of a ceiling fan blade including an embodiment of the present invention;

FIG. 2 is a side view of the ceiling fan blade of FIG. 1;

FIG. 3 is a back view of the ceiling fan blade of FIG. 1; and,

FIG. 4 is an end view of an embodiment of the present invention.

DESCRIPTION OF PREFERRED EMBODIMENTS

In the discussion of the Figures, the same numbers will be used to refer to the same or similar components throughout.

As well known to those skilled in the art, ceiling fans typically contain relatively large blades, which are moved at a relatively low velocity to provide air circulation in a room.

In FIG. 1, a ceiling fan blade 10 is shown. A pouch 12 having a front 14, a first side 16, a second side 18, a first end 20 and a second end 22 is positioned on blade 10 and retained in position by a strap 24. Pouch 12 comprises an open mesh material, which facilitates the flow of air through the open mesh as the ceiling fan blade is rotated. Desirably, at least the front, one end or one side are formed of the open mesh material. Desirably, the entire pouch may be formed of the open mesh material. The back 32 (shown in FIG. 2) may be a solid material but may also desirably be fabricated of the same open mesh material. The pouch is formed as a flexible walled pouch, which has an openable and closable opening 34, positioned on the front, a side, an end, or the back. In most instances, it will be preferred to locate the opening on the front, a side or an end.

The opening may be opened and closed by suitable system. For instance, a zipper may be used to open and close the opening, overlappable VELCRO® (trademark of Velcro, Inc. for hook and loop type fasteners) flaps may be used to open and close the opening, or other fasteners such as buttons, pressure sealable plastic grooves in plastic flaps and the like may be used. The opening may be fabricated of materials, which are biased toward a closed position so that it may e pulled open for use and allowed to return to a closed position.

The fragrant material may be any desired commercially available potpourri or like air freshener material. (Such materials typically comprise dried fragrant blossoms, plant components and the like. These materials may be placed in the pouch by accessing opening 34, placing the materials in the pouch and then closing the pouch. The pouch is then positioned on fan blade 10 and desirably on the top of fan blade 10 so that when blade 10 is rotated, air flows through the potpourri or other fragrant material contained in pouch 12. As noted previously, the opening may be on any side, end or the front or the back of pouch 12.

Desirably pouch 12 is retained in position on blade 10 by at least one strap 24. As shown in FIG. 3, two straps are used but it is not considered necessary that two straps be used, especially when the pouch is positioned on a top of blade 10. The straps may be joined by any suitable means such as buckles, hook and loop type fasteners and the like. A buckle 40 is shown in FIG. 3 and a hook and loop type fastener is shown by an overlapped end 38 on the second strap in FIG. 3. Desirably the straps are joined by hook and loop type fasteners positioned on the ends of straps 24. As shown in FIG. 4, straps 24 extend from either side of pouch 12 and are of a length suitable to be joined on back 36 of blade 10 to retain pouch 12 in position. VELCRO® hook and loop type fastener straps are greatly preferred since they permit ready engagement and disengagement and do not slip in engagement so that pouch 12 is readily retained on bladed 10 at any desired position. The degree of air flow through pouch 12 is readily varied by positioning pouch 12 nearer or further from an inner end 28 of blade 10 or nearer an outer end 26 of lade 10. This increases the air velocity substantially. Of course, the fan setting may be varied as well.

The mesh may be any suitable material and the mesh may be of any suitable size provided that the mesh is sufficiently large to permit free airflow through the mesh during operation of the fan and small enough to retain the air freshening material in the pouch. The mesh does not require great strength and can be of any suitable material. Desirably, the mesh is sufficiently small to prevent escape of particles of the potpourri or other freshener material through the mesh. If necessary, the potpourri or other freshener material could be screened to remove extremely fine materials prior to placing it in pouch 12.

In FIG. 3, the back side 36 of blade 10 is shown with straps 24 engaged. Ends 38 strap 24 are shown in engagement with the other ends of straps 24 via a hook and loop type fastener connection. While other connections could be used, hook and loop type fasteners are greatly preferred for the connection.

While the pouch is shown in position on top of the blade, the pouch may be positioned on either the top or the bottom of the blade. It is preferred that the pouch be positioned on top of the blade.

In tests of the present invention, it has been found that in many instances the desired degree of air freshening can be accomplished in a few minutes during normal operation of the fan. In such instances, it may be desirable to remove pouch 12 from the fan after a short period and seal it in a sealed container to preserve the air freshening material until it is desired to refresh the air in the room again.

The present invention provides an air freshener for attachment to a ceiling fan blade, which is very economical and very effective to disperse fragrances into the air in a room. This air freshener is extremely economical to use, permits the use of a wide variety of fragrances and is very easy to attach and remove from a ceiling fan blade.

Having thus described the present invention by reference to certain of its preferred embodiments, it is pointed out that the embodiments described are illustrative rather than limiting in nature and that many variations and modifications are possible within the scope of the present invention.

Having thus described the invention, I claim:

1. An air freshener for attachment to a ceiling fan blade, the air freshener comprising:
   a) a flexible walled pouch having a front and a back, a first and a second side, at least one of the first and second sides comprising an open mesh and a first and a second end, the pouch being adapted to contain a quantity of a particulate fragrant air freshening material of a particle size larger than openings in the open mesh;
   b) at least one retaining strap in restraining engagement with the pouch and extending around the ceiling fan blade and adapted to retain the pouch in a selected position on the ceiling fan blade, wherein the strap comprises strap portions extending on either side of the pouch, the strap portions being joinable about the fan blade to retain the pouch in a selected position on top of the fan blade; and
   c) an openable and closable opening in a least one of the front, back, first side, second side, first end and second end.

2. The air freshener of claim 1 wherein the pouch is retained in position on top of the fan blade.

3. The air freshener of claim 2 wherein the at least one retaining strap is in engagement with at least the front, the back, a side or an end of the pouch.

4. The air freshener of claim 2 wherein the at least one restraining strap is in restraining engagement with the back of the pouch.

5. The air freshener of claim 2 wherein a plurality of straps are used.

6. The air freshener of claim 2 wherein the air freshener is potpourri.

7. The air freshener of claim 1 wherein the front of the pouch comprises an open mesh.

8. The air freshener of claim 1 wherein at least one end of the pouch comprises an open mesh.

9. The air freshener of claim 1 wherein the closable opening is in at least one of the front, sides and ends.

10. The air freshener of claim 9 wherein the openable and closable opening is openable and closable by a zipper.

11. The air freshener of claim 9 wherein the openable and closable opening comprises overlapping hook and loop type fasteners.

* * * * *